United States Patent
Barreto et al.

(10) Patent No.: US 9,438,897 B2
(45) Date of Patent: Sep. 6, 2016

(54) METHOD AND APPARATUS FOR AUTOMATIC CAMERA CALIBRATION USING ONE OR MORE IMAGES OF A CHECKERBOARD PATTERN

(75) Inventors: João Pedro De Almeida Barreto, Coimbra (PT); Gabriel Falcão Paiva Fernandes, Figueira da Foz (PT); Rui Jorge Melo Teixeira, Coimbra (PT)

(73) Assignee: Universidade de Coimbra, Coimbra (PT)

( * ) Notice: Subject to any disclaimer, the term of this patent is extended or adjusted under 35 U.S.C. 154(b) by 96 days.

(21) Appl. No.: 14/234,907

(22) PCT Filed: Jul. 25, 2012

(86) PCT No.: PCT/PT2012/000030
§ 371 (c)(1),
(2), (4) Date: Apr. 28, 2014

(87) PCT Pub. No.: WO2013/015699
PCT Pub. Date: Jan. 31, 2013

(65) Prior Publication Data
US 2014/0285676 A1 Sep. 25, 2014

(30) Foreign Application Priority Data
Jul. 25, 2011 (PT) .......................................... 105832

(51) Int. Cl.
*H04N 17/00* (2006.01)
*H04N 5/232* (2006.01)
*H04N 5/225* (2006.01)

(52) U.S. Cl.
CPC ........ *H04N 17/002* (2013.01); *H04N 5/23293* (2013.01); *H04N 2005/2255* (2013.01)

(58) Field of Classification Search
CPC ........... H04N 17/002; H04N 5/23293; H04N 2005/2255
See application file for complete search history.

(56) References Cited

U.S. PATENT DOCUMENTS 7,751,865 B2  7/2010  Jascob
7,892,165 B2  2/2011  Nakamura
(Continued)

OTHER PUBLICATIONS

Rui Melo et al.: "A New Solution for Camera Calibration and Real-Time Image Distortion Correction in Medical Endoscopy Initial Technical Evaluation", IEEE Transactions on Biomedical Engineering, IEEE Service Center, Piscataway, NJ, USA, vol. 59, No. 3, Mar. 1, 2012, pp. 634-644, XP011416212.
(Continued)

*Primary Examiner* — Brian Yenke
*Assistant Examiner* — Sean Haiem
(74) *Attorney, Agent, or Firm* — Greenberg Traurig, LLP; David J. Dykeman; Andrew Abramson

(57) ABSTRACT

The present invention relates to a high precision method, model and apparatus for calibrating, determining the rotation of the lens scope around its symmetry axis, updating the projection model accordingly, and correcting the image radial distortion in real-time using parallel processing for best image quality.

The solution provided herein relies on a complete geometric calibration of optical devices, such as cameras commonly used in medicine and in industry in general, and subsequent rendering of perspective correct image in real-time. The calibration consists on the determination of the parameters of a suitable mapping function that assigns each pixel to the 3D direction of the corresponding incident light. The practical implementation of such solution is very straightforward, requiring the camera to capture only a single view of a readily available calibration target, that may be assembled inside a specially designed calibration apparatus, and a computer implemented processing pipeline that runs in real time using the parallel execution capabilities of the computational platform.

16 Claims, 14 Drawing Sheets

(56) References Cited

U.S. PATENT DOCUMENTS

| | | | |
|---|---|---|---|
| 8,223,193 B2 | 7/2012 | Zhao | |
| 2005/0085720 A1* | 4/2005 | Jascob | A61B 5/06 600/424 |
| 2005/0270375 A1* | 12/2005 | Poulin | G06T 7/0057 348/187 |
| 2005/0280709 A1* | 12/2005 | Katayama | G01C 11/02 348/187 |
| 2008/0075324 A1* | 3/2008 | Sato | G01B 11/2504 382/106 |
| 2008/0097156 A1* | 4/2008 | Nakamura | A61B 1/045 600/117 |
| 2010/0245541 A1* | 9/2010 | Zhao | G01D 1/00 348/45 |
| 2015/0254872 A1 | 9/2015 | Barreto et al. | |

OTHER PUBLICATIONS

Thomas Stehle et al.; "Dynamic Distortion Correction for Endoscopy Systems with Exchangeable Optics", Bilbverarbeitung Fur Die Medzin, Jan. 1, 2009, pp. 142-146, XP055045061.

Norio Fukuda et al.; "A scope cylinder rotation tracking method for oblique-viewing endoscopes without attached sensing device", Software Engineering and Data Mining (SEDM), 2010 $2^{nd}$ International Conference on, IEEE, Piscathaway, NJ, USA, Jun. 23, 2010, pp. 684-687, XP031728037.

International search report dated Nov. 22, 2012 in corresponding PCT Application No. PCT/PT2012/000030 filed Jul. 25, 2012.

Agrawal, A. et al., "Analytical Forward Projection for Axial Non-Central Diotropic and Catadioptric Cameras," presented at the ECCV'10: Proceedings of the 11th European Conference on Computer Vision: Part III, Sep. 2010.

Baker, S. et al., "A Spherical Eye from Multiple Cameras (Makes Better Models of the World)," IEEE Conf. Vis. Patt. Recogn., Feb. 2001.

Baker, S. et al., "Equivalence and Efficiency of Image Alignment Algorithms," IEEE Conf. Vis. Patt. Recogn., vol. 1, pp. 1090-1097, Dec. 2001.

Baker, S. et al.,"Lucas-Kanade 20 Years on: A Unifying Framework," Int. J. Comput. Vision, 56(3):221-255, Mar. 2004.

Baker, S. et al., "A database and Evaluation Methodology for Optical Flow," Int. J. Comput. Vision, 92(1), Dec. 2011.

Barreto, J. et al., "Automatic Camera Calibration Applied to Medical Endoscopy," BMVC, 2009.

Barreto, J. et al., "Ray-Based Calibration of Rigid Medical Endoscopes," OMNIVIS, 2008.

Barreto, J., "A Unifying Geomeetric Representation for Central Projection Systems," Comput. Vis. Image Underst., vol. 103, No. 3, pp. 208-217, 2006.

Behrens, A. et al., "Real-Time Image Composition of Bladder Mosaics in Fluorescence Endoscopy," Computer Science—Research and Development, 26:51-64, Feb. 2011.

Bouguet, J.-Y., Camera Calibration Toolbox for Matlab. [Online]. http://www.vision.caltech.edu/bouguetj/calibdoc/index.html#ref.

Bouget, J.-Y., "Pyramidal Implementation of the Lucas Kanade Feature Tracker Description of the Algorithm," 2000.

Brox, T. et al., "Large Displacement Optical Flow: Descriptor Matching in Variational Motion Estimation," IEEE Trans. Patt. Anal. Mach. Intell., 33(3):500-513, Mar. 2011.

Buck, S.D. et al., "Evaluation of a Novel Calibration Technique for Optically Tracked Oblique Laparoscopes," Proceedings of the 10th International Conference on Medical Image Computing and Computer-Assisted Intervention, vol. Part I, pp. 467-474, Feb. 2007.

Burschka, D. et al., "Scale-Invariant Registration of Monocular Endoscopic Images to CT-Scans for Sinus Surgery," Med. Image Comput. and Computer-Assist. Inter., Sep. 2004.

Carr, P. et al., "Point-less Calibration: Camera Parameters from Gradient-Based Alignment to Edge Images," Applications of Computer Vision (WACV), pp. 377-384, Jan. 9, 2012.

Chang, Y., "Multi-View 3D Reconstruction for Scenes Under the Refractive Plane with Known Vertical Direction," Computer Vision (ICCV), Nov. 2011.

Chapman, B. et al., "Using Open MP: Portable Shared Memory Parallel Programming" (Scientific Computation and Engineering Series) The MIT Press, 2008.

Claus, D. et al., "A Rational Function Lens Distortion Model for General Cameras," Computer Vision and Pattern Recognition IEEE Computer Society Conference on, pp. 213-219, vol. 1, Jun. 2005.

Daniilidis, K. et al., "Image Processing in Catadiop-tric Planes: Spaciotemporal Derivatives and Optical Flow Computation," Int. Workshop on Omndirectional Vision, Jun. 2002.

Fischler, M.A. et al., "Random Sample Consensus: A Paradigm for Model Fitting with Applications to Image Analysis and Automated Cartography," Commun. ACM, vol. 24, No. 6, pp. 381-395, 1981.

Fitzgibbon, A. et al., "Direct Least Square Filling of Ellipses," IEEE Transactions on Pattern Analysis and Machine Intelligence, vol. 21, No. 5, pp. 476-480, May 1999.

Fitzgibbon, A., "Simultaneous Linear Estimation of Multiple View Geometry and Lens Distortion," CVPR, vol. 1, pp. I-125-I-132, 2001.

Gauglitz, S. et al., "Evaluation of Interest Point Detectors and Feature Descriptors for Visual Tracking," Int. J. Comput. Vis., 94(3):335-360, Mar. 2011.

Hansen, P. et al., "Wide-Angle Visual Feature Matching for Outdoor Localization," Int. J. of Robot. Res., 29:267-297, Feb. 2010.

Helferty, J. "Videoendoscopic Distortion Correction and Its Application to Virtual Guidance of Endoscopy," IEEE Transactions on Medical Imaging, vol. 20, No. 7, pp. 605-617, Jul. 2001.

Hwangbo, M. et al., "Gyro-aided Feature Tracking for a Moving Camera: Fusion, Auto-Calibration and GPU Implementation,". Int. J. of Robot. Res., 30(14):1755-1774, Dec. 2011.

Kalman, R.E., et al., "A New Approach to Linear Filtering and Prediction Problems," ASME—Journal of Basic Engineering, 82 (Series D): 35-45; Mar. 1960.

Kim, D.S. et al., "Joint Optimization of Spatial Registration and Histogram Compensation for Microscopic Images," Conference Proceedings: Annual International Conference of the IEEE Engineering in Medicine and Biology Society; pp. 3779-3782; Aug. 30, 2006.

Kim, S.J. et al., "Joint Feature Tracking and Radiometric Calibration from Auto-Exposure Video," Computer Vision, pp. 1-8, Oct. 1, 2007.

Koeser, K. et al., "Robust GPU-Assisted Camera Tracking Using Free-Form Surface Models," Journal of Real-Time Image Processing, 2(2):133-147, Oct. 2007.

Lourenco, M. et al., "sRD-SIFT: Keypoint Detection and Matching in Images With Radial Distortion," IEEE Trans Robotics, Jun. 2012.

Lourenco, M. et al., "Tracking Features in Uncalibrated Images with Radial Distortion," Eur. Conf. Comput. Vis., pp. 1-14, Oct. 2012.

Lucas, B.D. et al., "An Iterative Image Registration Technique with an Application to Stereo Vision," DARPA Image Understanding Workshop, pp. 121-130, Apr. 1981.

Mallon, J. et al., "Which Pattern? Biasing Aspects of Planar Calibration Patterns and Detection Methods," Pattern Recognition Letters, vol. 28, pp. 921-930, Jan. 2007.

Matthews, L. et al., "The Template Update Problem," IEEE Trans. Patt. Anal. Mach. Intell., 26(6):810-815, Jun. 2004.

Mei, C. et al., "Constrained Multiple Planar Template Tracking for Central Catadioptric Cameras," British Machine Vision Conference, Sep. 2006.

Mei, C. et al., "Efficient Homography-based Tracking and 3D Reconstruction for Single Viewpoint Sensors," IEEE Trans Robotics, Dec. 2008.

Menem, M., "Constraints on Perspective Images and Circular Panoramas," BMVC, Sep. 2004.

Nister, D. et al., "An Efficient Solution to the Five-Point Relative Pose Problem," IEEE Trans. Patt. Anal. Mach. Intell., 26, Jun. 2004.

Pollefeys, M. et al., "Visual Modeling with a Hand-Held Camera," Int. J. Comput. Vis., 59(3):207-232, Sep. 2004.

Rav-Acha, A. et al., "Lucas-Kanade without Iterative Warping," IEEE Int. Cont. Image Process., pp. 1097-1100, Oct. 2006.

(56) References Cited

OTHER PUBLICATIONS

Salazar-Garibay, A. et al., "Visual Tracking of Planes with an Uncalibrated Central Catadioptric Camera," IROS, Mar. 2009.

Shahidi, R., et al., "Implementation, Calibration and Accuracy Testing of an Image-Enhanced Endoscopy System," IEEE Transactions on Medical Imaging, vol. 21, No. 12, pp. 1524-1535, Dec. 2002.

Shi, J. et al., "Good Features to Track," IEEE Conf. Vis. Patt. Recogn., pp. 593-600, Jun. 1994.

Smith, W. et al., "Correction of Distortion in Endoscope Images," IEEE Transactions on Medical Imaging, vol. 11, No. 1, pp. 117-122, Jan. 1992.

Song, K.S. et al., "Region Adaptive Correction Method for Radial Distortion of Fish-Eye Image," Image Processing: Algorithms and Systems X; and Parallel Processing for Imaging Applications II, SPIE, vol. 8295, No. 1., pp. 1-7, Feb. 9, 2012.

Sturm, P. et al., "Camera Models and Fundamental Concepts Used in Geometric Computer Vision," Now Publishers, Inc., Jan. 2011.

Tamaki, T. et al., "Unified Approach to Image Distortion," ICPR, pp. 584-587, Aug. 2002.

Triggs, B. et al., "Bundle Adjustment—A Modem Synthesis," Proceedings of the International Workshop on Vision Algorithms: Theory and Practice, ICCV '99, pp. 298-372, London, UK, Springer-Verlag, 2000.

Vijayan-Asari, K. et al., "A New Approach for Nonlinear Distortion Correction in Endoscopic Images Based on Least Squares Estimation," IEEE Transactions on Medical Imaging, vol. 18, No. 4, pp. 345-354, Apr. 1999.

Welch, G. et al., "An Introduction to the Kalman Filter," Technical Report, University of North Carolina at Chapel Hill, Chapel Hill, N.C., USA, 1995; updated Jul. 2006.

Wengert, C. et al., "Fully Automatic Endoscope Calibration for Intraoperative Use," Bildverarbeitungfür die Medizin, pp. 419-423, Mar. 2006.

Willson, R.G. et al., "What is the Center of the Image?" J. Opt. Soc. Am. A, 11(11):2946-2955, Apr. 1991.

Wu, C. et al., "A Full Geometric and Photometric Calibration Method for Oblique-viewing Endoscope," International Journal of Computer Aided Surgery, vol. 15, pp. 19-31, 2010.

Yamaguchi, T. et al., "Camera Model and Calibration Procedure for Oblique-Viewing Endoscope," MICCAI, pp. 373-381, 2003.

Yilmaz, A. et al., "Object Tracking: A Survey," ACM Comput. Surv., 38, Dec. 2006.

Zhang, Z., "Flexible Camera Calibration by Viewing a Plane from Unknown Orientations," ICCV, pp. 666-673, Sep. 1999.

Hartley, R. et al., "Parameter-free radial distortion correction with center of distortion estimation," IEEE Trans Pattern Analysis and Machine Intelligence, vol. 29, No. 8, pp. 1309-1321, 2007.

Zhang, Z. "A flexible new technique for camera calibration". IEEE Transactions on Pattern Analysis and Machine Intelligence, 22(11):1330-1334, 2000.

* cited by examiner

TABLE I
CALIBRATION PARAMETERS COMPARISON BETWEEN SIC AND BOUGUET CALIBRATION TOOLBOX.

| | $c_x$ | $c_y$ | $f$ | $\xi$ |
|---|---|---|---|---|
| SIC (mean) | 595.77 | 500.14 | 558.88 | -0.527 |
| SIC (std) | 7.069 | 4.889 | 34.935 | 0.0066 |
| Bouguet | 599.32 | 497.08 | 541.90 | -0.497 |

Figure 11

TABLE II

EXECUTION TIMES, IN MILLISECONDS, AND FRAMES PER SECOND (*fps*) ACHIEVED WITH THE FULL SYSTEM RUNNING THE OPTIMIZED HYBRID CPU+GPU SOLUTION FOR DIFFERENT IMAGE RESOLUTIONS.

| Input size | Output size | I.C. | B.E. | R.D.C. | Total (ms) | fps |
|---|---|---|---|---|---|---|
| 640x480 | 700x700 | 2.53 | 3.48 | 2.51 | 8.52 | 117 |
| 640x480 | 1500x1500 | 2.51 | 3.15 | 7.92 | 13.58 | 74 |
| 1280x960 | 2000x2000 | 9.38 | 4.52 | 13.52 | 27.41 | 36 |
| 1280x960 | 3000x3000 | 9.37 | 5.36 | 28.21 | 42.94 | 23 |
| 1600x1200 | 2200x2200 | 11.86 | 5.02 | 17.22 | 34.11 | 30 |
| 1600x1200 | 4000x4000 | 11.72 | 4.88 | 51.39 | 67.99 | 15 |
| 2448x2048 | 3000x3000 | 30.27 | 11.89 | 32.07 | 74.23 | 13 |
| 2448x2048 | 5000x5000 | 30.17 | 12.46 | 79.88 | 122.51 | 8 |

Figure 12

METHOD AND APPARATUS FOR AUTOMATIC CAMERA CALIBRATION USING ONE OR MORE IMAGES OF A CHECKERBOARD PATTERN

CROSS REFERENCE TO RELATED APPLICATIONS

This application is a 371 application of International Application No. PCT/PT2012/000030, filed Jul. 25, 2012, which claims priority to Portuguese Patent Application PT105832, filed Jul. 25, 2011, all of which are incorporated by reference in its entirety herein.

FIELD OF INVENTION

The present invention relates to a high precision method, model and apparatus for calibrating, determining the rotation of the lens scope around its symmetry axis, updating the projection model accordingly, and correcting the image radial distortion in real-time using parallel processing for best image quality.

BACKGROUND OF THE INVENTION

An optical instrument is generally required to produce a geometrically consistent image of a given object, where each point in 3D is projected into a point in the image. The image is generally formed in accordance with some predefined imaging model, which in this case, it is assumed to be a pin-hole model. The departure of practical optical systems from ideal behavior leads to the introduction of aberrations in the resulting images. The aberration here is lens distortion, which is present in both color and grey-scale imaging devices. Its nature is predominantly a radial geometric displacement of pixels, giving a barrel or a pincushion effect. Lens distortion is a thorn in the side of many relatively straightforward image analysis tasks. It comprehensively degrades the accuracy of measurements made in real images, where pixels in a normal perspective camera can suffer large displacements along the radial directions. Moreover, it also affects the visual perception, namely by changing depth cues.

One known method for addressing lens distortion is in conjunction with a complete calibration of the camera system. Complete camera calibration essentially means that the camera's internal and external parameters are obtained [8]. Many applications do not require the full complement of internal camera parameters and the relative orientation in relation to some calibration target. Non-metric applications differ in that the distortion is determined without necessarily estimating the entire camera internal and external parameters.

In the 1960's Duane C. Brown, working in the area of photogrammetry, proposed a method for determining lens distortion based on the truism that straight lines must be imaged as straight lines. This technique, published in (Brown, 1971), and with extensions in (Fryer and Brown, 1986), became known as the 'plumb line' method. A comprehensive historical review is given in Clarke and Fryer (1998). This technique was adopted by the machine vision community where simplified versions of the plumb line method were presented, e.g. Prescott and McLean (1997b), (also as patent Prescott and McLean (1997a) XP000683415) Haneishi et al. (1995a) (also as patent Haneishi et al. (1995b) XP000527216) Poulo and Gorman (1999) U.S. Pat. No. 6,002,525 and Asari et al. (1999) all describe a similar truism for the correction of distortion using images of co-linear points. Since these methods only estimate distortion, they are sometimes referred to as non-metric calibration.

An intrinsic problem for "plumb line" based calibration is that the optimization/search must be run with respect to both the straight line parameters (that are unknown) and the distortion parameters (that are also unknown). An alternating approach was employed, for example in Devernay and Faugeras (2001), Tzu-Hung (2003) and Bing (1999) EP0895189, which iteratively adjusts the distortion parameters in order to minimize the line fitting to the distorted line segments. No sufficiently validated mathematical relationship exists between the objective error and the distortion parameters, hence no analytical derivatives are available. These results in slow convergence and can become unstable for elevated distortion levels, unless special steps are taken, as in Swaminathan and Nayar (2000). In this non-metric approach Swaminathan and Nayar (2000) reformulated the objective function in distorted space instead of the usual undistorted space.

Another approach has been suggested in Ahmed and Farag (2001) where the curvature of detected lines is used to estimate the parameters of the derivative distortion equation. However, the simulation results showed abysmal performance in the presence of noise, while the real results lacked a quantitative evaluation.

A more standard manner of calibrating distortion is with the simultaneous estimation of a camera's extrinsic and intrinsic parameters. Tsai's method (Tsai, 1987) involves simultaneously estimating, via an iterative numerical optimization scheme, the single distortion parameter and some internal parameters such as focal length, given the 3D position of a set of control points. The disadvantage of this approach is that it requires known 3D control points and in return offers relatively low accuracy for all but simple distortion profiles. Algorithmic variations on this principal have been proposed by several authors, such as Weng et al. (1992) and Wei and Ma (1994) using more appropriate models for lens distortion. These methods also require known 3D control points.

The rendering of distortion corrected images is investigated in Heikkila and Silven (1997), wHeikkila (2000) describing a similar technique that requires 3D control points or multiple image sets of 2D control points. An alternative method also based on multiple sets of 2D control points has been advanced in Zhang (1998, 2000) and Sturm and Maybank (1999). This technique addresses distortion through an alternating linear least squares solution, which is then iteratively adjusted in a numerical minimization including all estimation parameters. The relative complexity of these techniques is increased by the inclusion of lens distortion.

On the other hand there are many situations where only distortion removal is required, not the full complement of intrinsic and extrinsic parameters. An example is in the estimation of multiple view geometry in real images, where techniques have been specifically developed to accommodate lens distortion. Zhang (1996) investigates the possibility of simultaneously estimating distortion parameters and the Fundamental Matrix. The results conclude that this is possible if noise is low and distortion is high. Fitzgibbon (2001) (with patent Fitzgibbon (2003) GB2380887), Micusik and Pajdla (2003) and Barreto and Daniilidis (2004) use an alternative model for distortion, leading to a polynomial Eigen value problem, and a more reliable estimation of distortion and geometry. Stein (1997) took the reverse approach and used the error in Fundamental Matrix estimation as an objective error to estimate distortion parameters.

Alternative methods of distortion calibration exist, where control points correspondences are abandoned in favor of distortion free scenes. These scenes are then imaged by the camera system, whereupon an image alignment process is conducted to correct for distortion. Lucchese and Mitra (2003) describe a technique where the distorted image is warped until it registers (in intensity terms) with the reference image. A similar technique using a coarse filter to find registration is described in Tamaki (2002) (with patent Tamaki et al. (2002) US2002057345) while Sawhney and Kumar (1999) (also with patent Kumar et al. (1998) WO9821690) describe a registration technique that does not require an undistorted reference image. Instead, multiple images are registered for the generation of a mosaic image, for example such as a panoramic resulting from the combination of several different views, and distortion is simultaneously estimated. These techniques have a very high computational overhead, with twenty minutes quoted in Tamaki (2002).

A final class of non-metric calibration methods are based on distortion induced high-order correlations in the frequency domain. Farid and Popescu (2001) describe a technique, however its performance is poor in comparison with regular camera calibration techniques, and it also appears to be slightly dependent on the image content. Yu (2004) further develops this approach with alternative distortion models and reports accuracy approaching that achieved with regular camera calibration if the source image is of a regular calibration target. Finally, a means of fabricating a curved CCD array has been suggested by Gary (2003) US2003141433. The lens distortion profile is copied in the array by a series of line segments, thus the resulting image appears distortion free.

SUMMARY

The solution provided herein relies on a complete geometric calibration of optical devices, such as cameras commonly used in medicine and in industry in general, and subsequent rendering of perspective correct image in real-time. The calibration consists on the determination of the parameters of a suitable mapping function that assigns each pixel to the 3D direction of the corresponding incident light. The practical implementation of such solution is very straightforward, requiring the camera to capture only a single view of a readily available calibration target, that may be assembled inside a specially designed calibration apparatus, and a computer implemented processing pipeline that runs in real time using the parallel execution capabilities of the computational platform.

The invention refers as well as to a computer program embodied on a computer medium which, when executed by a processor, performs all the method steps.

A more complete understanding of the invention will be appreciated from the description and accompanying drawings and the claims, which follow.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 11 shows the calibration parameters comparison between SIC and bouguet calibration toolbox.

FIG. 12 shows the execution times, in milliseconds, and frames per second (fps) achieved with the full system running the optimized hybrid CPU+GPU solution for different image resolutions.

DETAILED DESCRIPTION

Figure 14:
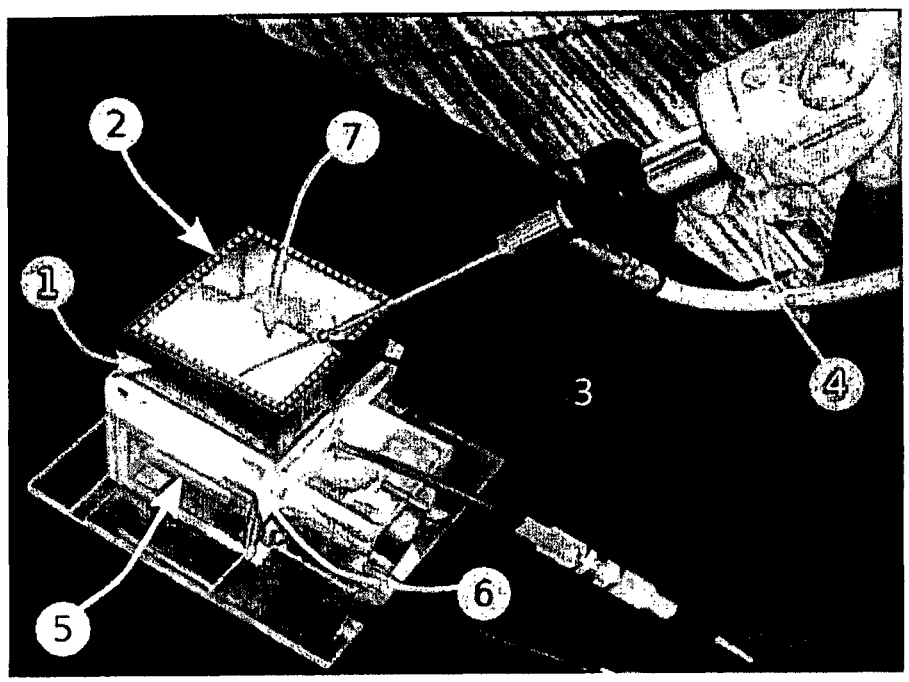
FIG. 14 shows the calibration box schematic. (1)—box upper compartment built using opaque, waterproof materials for avoiding the entrance of light from the exterior; (2)—openings for giving access to the lens probe; (3)—opaque material membrane that minimizes the entrance of light from the exterior; (4)—image acquisition device; (5)—lower compartment o the box, where the diffuse light source is installed; (6)—separator between the lower and upper compartments; (7)—planar grid with a known pattern, made of transparent or translucent material, which is placed on the top of the separator.
Figure 14:
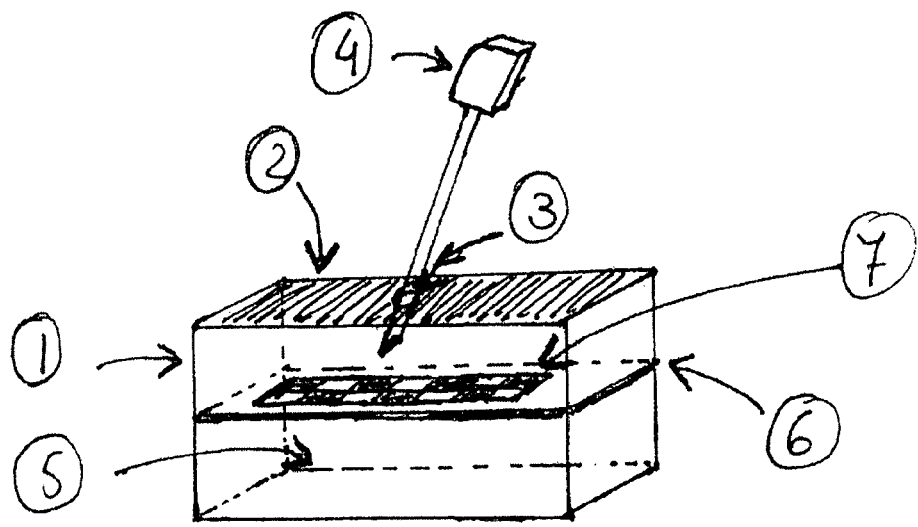

We propose a complete solution for the calibration, online updating of the projection parameters in case of lens rotation, and radial distortion correction in real-time. The solution comprises the modules and blocks shown in the scheme in FIG. 3 and the apparatus of FIG. 14, being that the operator starts by acquiring a single image of a checkerboard pattern using the setup in FIG. 2.

The system herein presented was originally meant for medical endoscopy that typically employs a boroscopic lens probe mounted on a standard CCD camera. However, our solution is extendable to other application domains using cameras with significant radial distortion that might benefit from accurate geometric calibration and real-time image correction. Examples of these domains include surveillance, industrial inspection, automotive, robot navigation, etc, that often rely in images/video acquired by cameras equipped fish-eye lenses, wide angular lenses, mini lenses, or low quality optics.

The apparatus that is disclosed in this patent application consists of a calibration box (FIG. 14) used to acquire a single image of a known pattern. The acquired image is used as input to the novel calibration algorithm (FIG. 13), that will provide the necessary camera parameters to perform a real-time and lens rotation independent image distortion correction.

Figure 1:
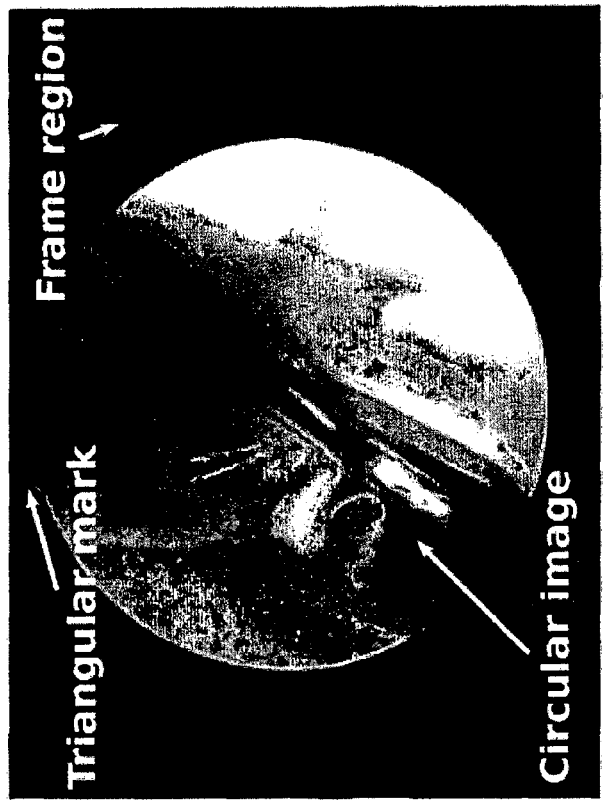
FIG. 1 shows the rigid medical endoscope that combines a borescope with a CCD camera (a). The system enables the visualization of human body cavities whose access is difficult or limited, and is widely used for both surgery and diagnosis. (b) is an image of the interior of a knee joint, acquired by a 30° oblique viewing arthroscope.
Figure 1:
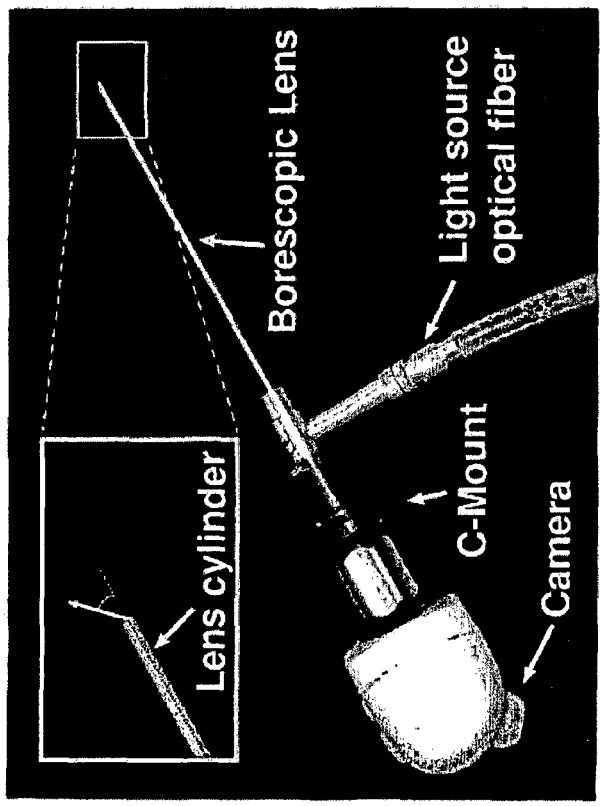
Figure 2:
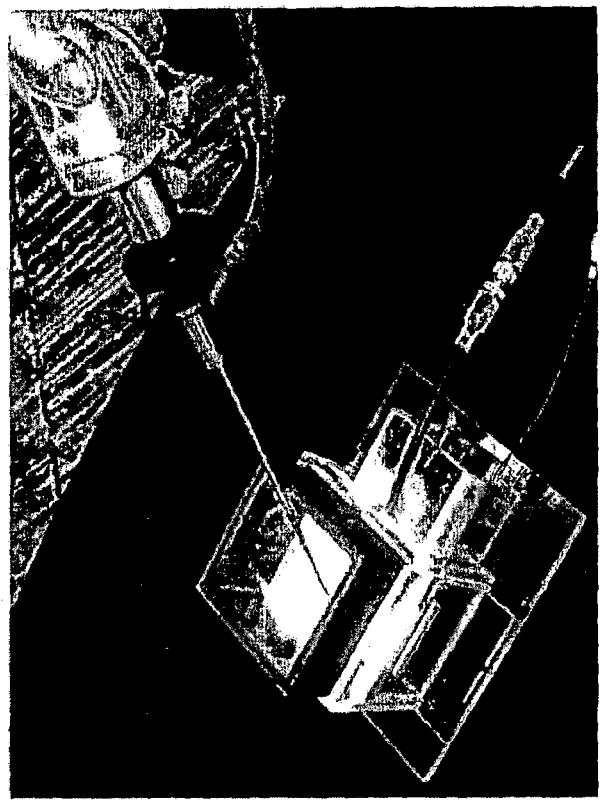
FIG. 2 shows the calibration of the endoscopic camera from a single image of a planar checkerboard pattern. The calibration image of (a) is acquired in an unconstrained manner (no assumptions about the relative pose between camera and plane) using the setup shown in (b). The exhibited setup consists of an acrylic box that controls the lighting conditions. The planar grid is backlit to enable the robust and accurate detection of the image corners without user intervention.
Figure 2:
Figure 3:
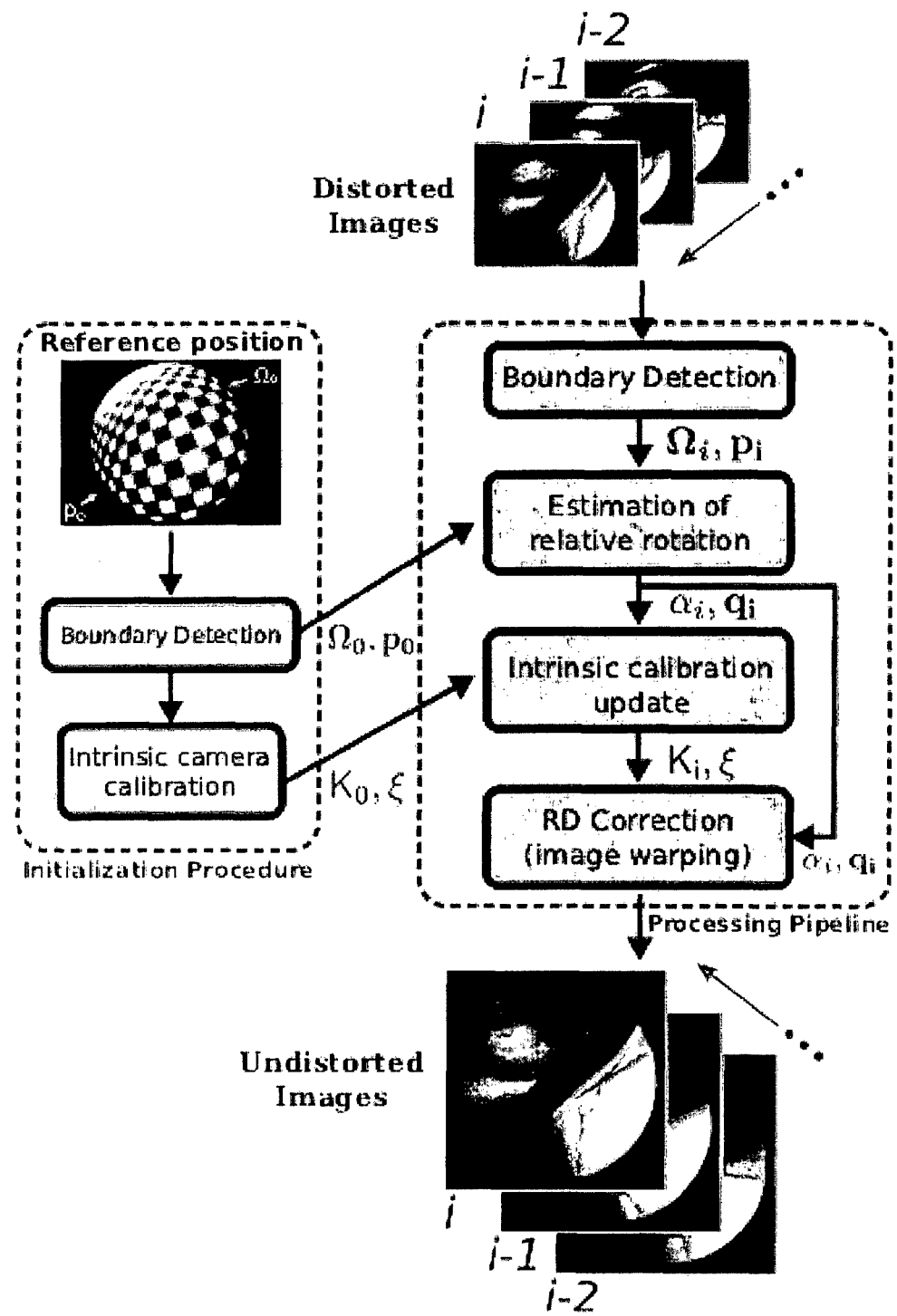
FIG. 3 is the scheme showing the different modules of the system that is proposed for calibrating the camera and correcting the radial distortion of the images/video. The left-hand side concerns the Initialization Procedure that is performed only once, after connecting the endoscopic lens to the CCD camera, and requires the acquisition of a single calibration image using the setup in FIG. 2. The right-hand side shows the Processing Pipeline that is executed at each frame time instant i in order to correct the radial distortion in the endoscopic video stream.
Figure 4:
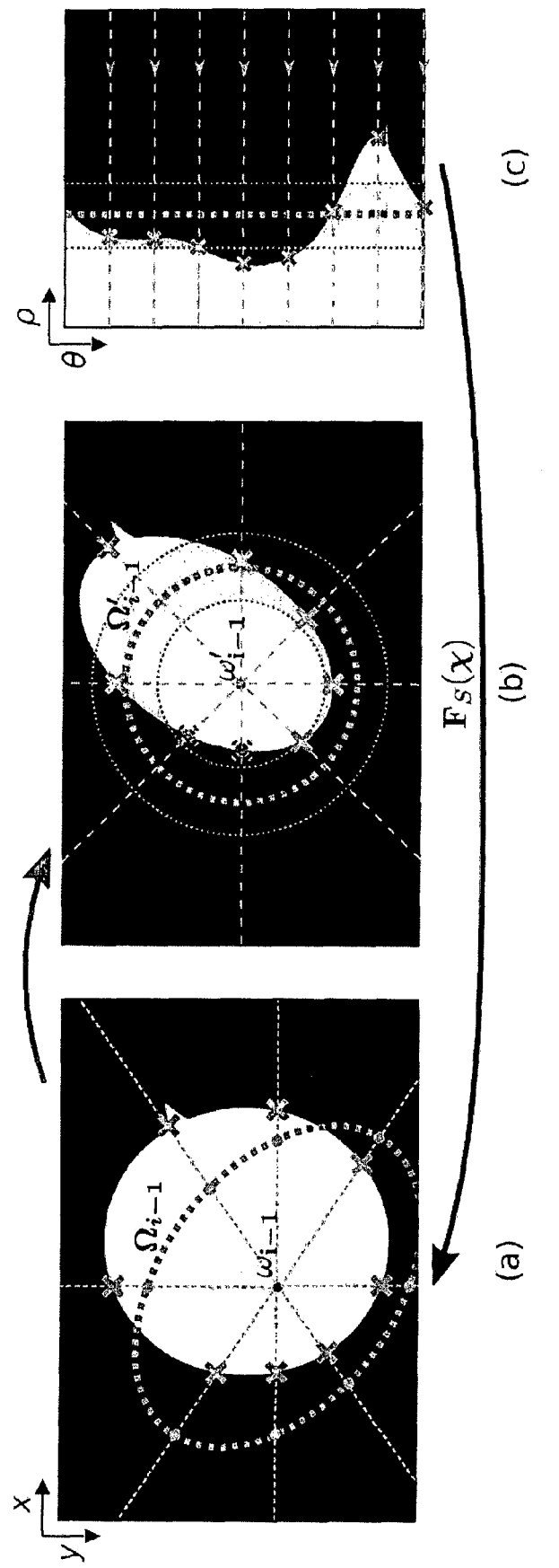
FIG. 4 shows the tracking of the boundary contour. The schemes from left to the right relate to the original frame acquired at time instant i, the warped image using the affine transformation S, and the polar image obtained by changing from Cartesian to spherical coordinates. The red dashed overlay relates to the previous boundary estimate, and the crosses are the detected points in the current contour. S maps $\Omega_{i-1}$ into a unit circle. The purple shaded area is the image region that suffers the polar warp and is where the search is performed.
Figure 5:
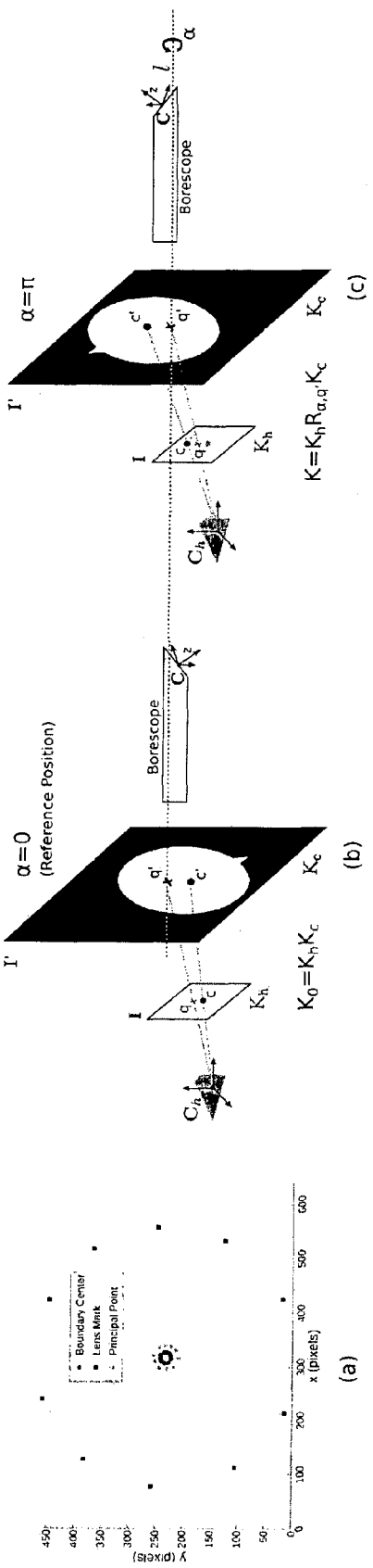
FIG. 5 shows (a) a plot of the principal point c, triangular mark p, and boundary center w, when the lens undergoes a full rotation. (b) and (c) illustrates the model and assumptions that are considered for updating the intrinsic matrix of the endoscopic camera. The lens projects a virtual image onto a plane l' that is imaged into l by a CCD camera. The relative rotation of the lens is around an axis l that is parallel to the optical axis and orthogonal to planes l and l'. c represents the principal point and q is the center of the induced image rotation.
Figure 6:
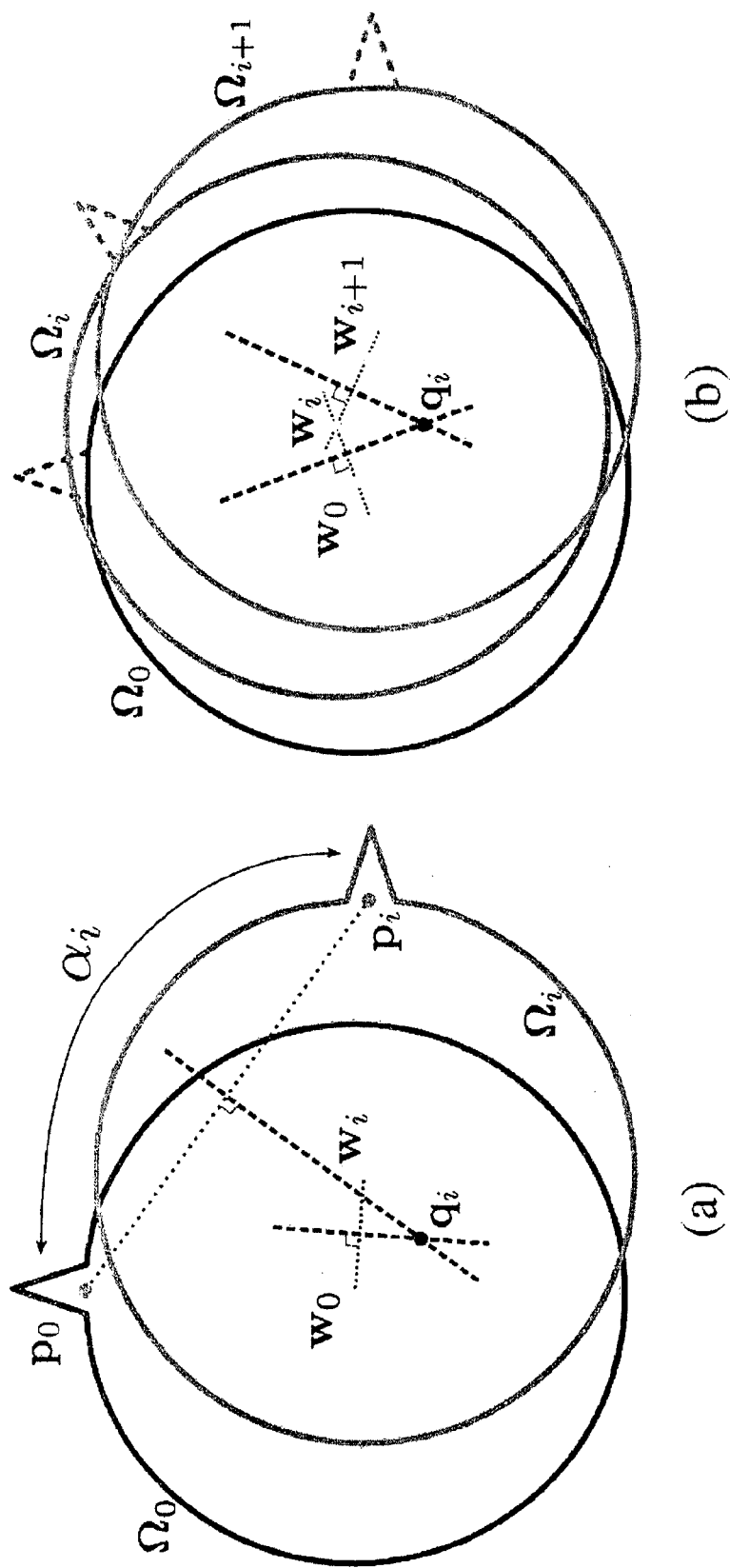
FIG. 6 shows the computation of the image rotation center $q_i$ when the triangular mark is correctly detected (a), and when there is no mark information (b).
Figure 13:
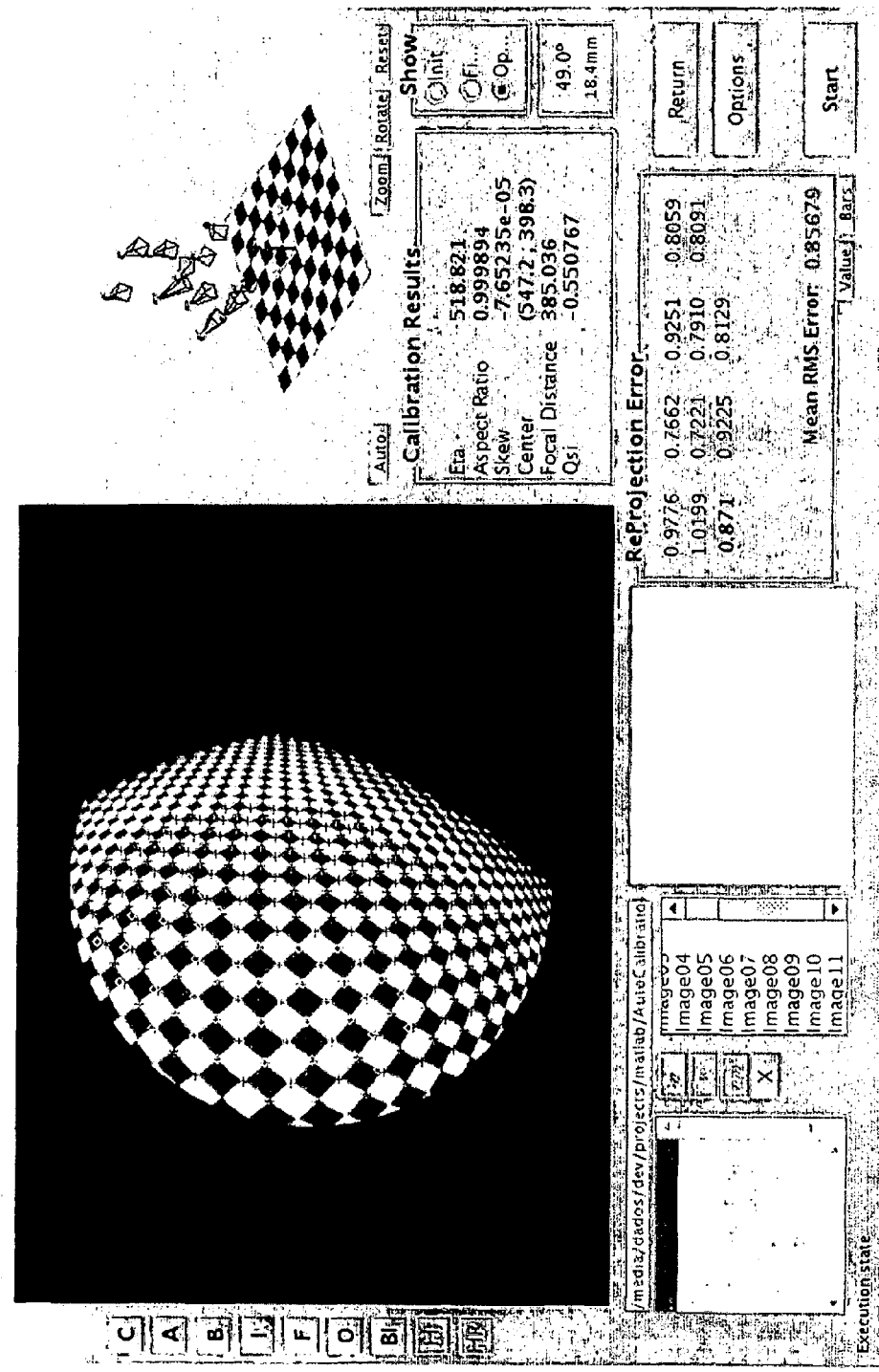
FIG. 13 shows the calibration from a single image (software screenshot).

The calibration images are acquired using a box built using opaque materials for avoiding the entrance of light from the exterior (FIG. 13). The box has one or more openings for giving access to the lens probe (FIG. 13-3), and each opening is surrounded by a rubber membrane that minimizes the entrance of light from the exterior (FIG. 13-2). The box is divided in two compartments by a separator in transparent or translucent material (FIG. 13-6). A planar grid with a known pattern (FIG. 13-7), made of transparent or translucent material, is placed in the upper compartment (FIG. 13-1) on the top of the separator. A light source, for diffuse back-illumination of the planar grid, is placed in the lower compartment (FIG. 13-5). The upper compartment can be filled with a fluid for better replicating the mean where the visual inspection will be carried. The apparatus comprises a computer unit, with sequential and parallel processing capabilities, such as a Central Processing Unit and a Graphics Processing Unit, which is connected to a camera for image acquisition (FIG. 13-4). A display and an interface device connected to the computer unit are also required for visualizing and entering user commands.

The method for automatic camera calibration, on-line update of the projection parameters in case of lens rotation, and real-time image rectification/correction using parallel processing, is summarized as follows: The corners in the calibration frame are detected, and both the camera intrinsic $K_0$ and the radial distortion $\xi$ are estimated without further user intervention. After this brief initialization step the processing pipeline on the right of FIG. 3 is executed for each acquired image. At each frame time instant i we detect the boundary contour $\Omega_i$, as well as the position of the triangular mark $p_i$. The detection results are used as input in an estimation filter which, given the boundary $\Omega_0$ and marker position $p_0$ in the calibration frame, then estimates the relative image rotation due to the possible motion of the lens probe with respect to the camera head. This 2D rotation is parameterized by the angle αi and the fixed point qi that serve as input for updating the camera calibration based on a new adaptive projection model. Finally, the current geometric calibration $K_i$, $\xi$ is used for warping the input frame and correct the radial distortion. This processing pipeline runs in real time with computationally intensive tasks, like the image warping and the boundary detection, being efficiently implemented using the parallel execution capabilities of the GPU.

A. Aquisition of One or More Images of a Checkerboard Pattern.

User intervention is limited to the acquisition of one or more calibration images using the calibration box of FIG. 2(b), which is detailed in FIG. 13. The pose of the camera with respect to the checkerboard plane is arbitrary, and the box of FIG. 13 is meant for controlling the illumination conditions for the automatic detection of image corners. The image acquired is similar to FIG. 2(a).

B. Detection of Grid Corners in the Calibration Image and Establishment of Image-Plane Correspondances It is important to note that locating corners in an image with strong radial distortion can be highly problematic because of the bending of the straight lines. After the frame acquisition the processing steps are:

1) Localization of a minimum of 12 corners in the center image region where the distortion is less pronounced. This operation is carried out by a heuristic algorithm that uses standard image processing techniques. The consistent correspondence between image corners x and grid points g is accomplished by counting the squares of the checkerboard pattern.

2) The image-plane correspondences are used for estimating the function that maps points in planar grid coordinates into points in image coordinates, this is, estimate $\hat{H}_{6\times6}$ using a DLT-like approach (equation 7 in section B).

3) The checkerboard pattern is projected onto the image plane using the homography for generating corner hypotheses in the image periphery. These hypotheses are confirmed and refined by applying a standard image corner finder.

4) The steps 2) and 3) are iterated until the number of established correspondences is considered satisfactory.

C. Determination of the Camera Intrinsic Parameters Using the Image-Plane Correspondences in at Least One Calibration Image.

The purpose of the Initialization Procedure in FIG. 3 is to determine the intrinsic calibration matrix $K_0$ and the radial distortion $\xi$ when the lens probe is at a reference position $\Omega_0$, $p_0$. Camera calibration is a well-studied topic with hundreds of references in the literature. The most widely used software is probably Bouguet's toolbox [16] that implements Zhang's method [17] for calibrating a generic camera from a minimum of 3 images of a planar grid. Unfortunately, the Bouguet toolbox does not meet the usability requirements of our application. In practice the number of input images for achieving accurate results is way above 3, and the detection of grid corners in images with RD needs substantial user intervention. Our method works with a minimum of one image.

Several authors have addressed the specific problem of intrinsic calibration of medical endoscopes [9]-[11], [18], [19]. However, these methods are either impractical for use in the OR or they employ circular dot patterns to enable the automatic detection of calibration points, which undermines the accuracy of the results [20].

A camera equipped with a borescope is a compound system with a complex optical arrangement. The projection is central [5] and the image distortion is described well by the so-called division model [21], [14], [13].

Barreto et al. show that a camera following the projection model described above can be calibrated from a single image of a planar checkerboard pattern acquired from an arbitrary position [21]. Let g be a point in the checkerboard expressed in plane homogeneous coordinates, x is the corresponding point in the image plane and H is the homography encoding the relative pose between plane and camera [8]. A point g in the checkerboard plane is mapped into the image through the following function:

$$x \sim K_0 \Gamma_\xi(Hg). \tag{}$$

Where $\Gamma_\xi$ is a nonlinear projective function that accounts for the image radial distortion [21], and $K_0$ is the matrix of intrinsic parameters with the following structure:

$$K_0 \sim \begin{pmatrix} af & sf & c_x \\ 0 & a^{-1}f & c_y \\ 0 & 0 & 1 \end{pmatrix} \tag{3}$$

Where f, a, and s, stand respectively for the focal length, aspect ratio, and skew, and $c=(c_x,c_y)^T$ are the non-homogeneous coordinates of the image principal point.

Let $\hat{g}$ and $\hat{x}$ be homogeneous vectors with dimension 6 corresponding to the lifted representation of points g and x according to a second order Veronese map [13]. It can be proved that $$\hat{x} \sim \hat{H}_{6 \times 6} \hat{g} \tag{7}$$

With $\hat{H}_{6 \times 6}$ being a 6×6 matrix. Since each image-plane correspondence imposes 3 linear constraints on the lifted homography, the matrix $\hat{H}_{6 \times 6}$ can be estimated from a minimum of 12 point correspondences (x,g) using a Direct Linear Transformation (DLT)-like approach. Given $\hat{H}_{6 \times 6}$, the matrix of intrinsic parameters $K_0$, the distortion parameter $\xi$, and the original homography H, can be factorized in a straightforward manner. This initial camera calibration can be further refined using standard iterative non-linear optimization.

D. Boundary Contour Detection Between Circular and Frame Regions

Finding the image contour that separates circular and frame regions (see FIG. 1(b)) is important not only to delimit meaningful visual contents, but also to infer the rotation of the lens probe with respect to the camera head. The proposed approach for tracking the boundary contour and the triangular mark across successive frames is related to work by Fukuda et al. [4] and Stehle et al. [15]. The first infers the lens rotation in oblique viewing endoscopes by extracting the triangular mark using conventional image processing techniques. The method assumes that the position of the circular region does not change during operation, which is in general not true, and it is unclear if it can run in real time. Stehle et al. proposes tracking the boundary contour across frames by fitting a conic curve to edge points detected in radial directions. The main difference from our algorithm is that we use a hybrid serial+parallel implementation for rendering a polar image and carry out the search along horizontal lines. This strategy makes it possible to reconcile robustness and accuracy with low computational cost.

Since the lens probe moves with respect to the camera head the contour position changes across frames, which precludes using an initial off-line estimation. The boundary detection must be performed at each frame time instant, which imposes constraints on the computational complexity of the chosen algorithm. Several issues preclude the use of naive approaches for segmenting the circular region: the light often spreads to the frame region; the circular image can have dark areas, depending on the imaged scene and lighting conditions; and there are often highlights, specularity, and saturation that affect the segmentation performance.

It is reasonable to assume that the curve to be determined is always an ellipse $\Omega$ with 5 degrees of freedom (DOF) [8]. Thus, we propose to track the boundary across frames using this shape prior to achieve robustness and quasi-deterministic runtime. Let $\Omega_{i-1}$ be the curve estimate at the frame time instant i-1 as shown in FIG. 4(a). The boundary contour for the current frame i is updated as follows:

1) Definition of a ring area in the original image (FIG. 4(b)), partially or totally containing the last estimate of the boundary.
2) Rendering of a new stripe image where the previous boundary estimate is mapped into the central vertical line (FIG. 4(c)). It is well known that there is always an affine transformation that maps an arbitrary ellipse into a unitary circle whose center is in the origin [8]. Such transformation S is given by:

$$S \sim \begin{pmatrix} r\cos(\phi) & r\sin(\phi) & -r(w_{i-1,x}\cos(\phi) + w_{i-1,y}\sin(\phi)) \\ -\sin(\phi) & \cos(\phi) & w_{i-1,x}\sin(\phi) - w_{i-1,y}\cos(\phi) \\ 0 & 0 & 1 \end{pmatrix},$$

where r is the ratio between the minor and major axis of $\Omega_{i-1}$, $\phi$ is the angle between the major axis and the horizontal direction, and $(w_{i-1,x}, w_{i-1,y})$ are the non-homogeneous coordinates of the conic center $w_{i-1}$. The transformation S is used to generate the intermediate result of FIG. 4(b), and the polar image (FIG. 4(c)) is obtained by applying a change from Cartesian to spherical coordinates.

3) Detection of boundary points in the stripe image using image processing techniques. The edge points in the stripe image of FIG. 4(c) are detected by applying a 1-dimensional edge filter (such as Laplacian of Gaussian) and scanning the horizontal lines from the right to the left to find the transition.
4) The edge points, which are expressed in spherical coordinates $x=(\rho, \theta)$, are mapped back into the original image points by the function $F_S$ of equation 1.

$$x \sim F_S(\chi) \sim S^{-1} \begin{pmatrix} \rho\cos(\theta) \\ \rho\sin(\theta) \\ 1 \end{pmatrix}, \quad (1)$$

The current conic boundary Qi is finally estimated using the robust conic fitting [23] and using RANSAC [24] to avoid the pernicious effects of possible outliers.
5) The steps from 1) to 4) are repeated until the boundary contour estimate converges.

The steps presented to estimate the boundary contour of the circular image are accelerated using the parallel processing capabilities of the computational unit.

E. Estimation of the Angular Displacement of the Lens Probe Relatively to the Camera when the Lens Undergoes Rotation Motion After correct convergence of the method described in section D, the boundary contour is mapped into the central vertical line of the polar image (FIG. 4(c)), enabling the robust detection of the triangular mark by scanning an auxiliary vertical line slightly deviated to the right, and selecting the pixel location that has maximum intensity. The position of the triangular mark is fed into a stochastic filter that infers the current angular displacement relatively to the calibration position at each frame.

F. Update of the Projection Model for the Current Frame Based on the Calibration and Angular Displacement of the Lens Probe The relative motion between lens and camera head causes changes in the calibration parameters that prevent the use of a constant model for correcting the distortion [5]. There is a handful of works proposing solutions for this problem [2]-[4], [15], [22], but most of them have the drawback of requiring additional instrumentation for determining the lens rotation [2], [3], [22]. The few methods relying only on image information for inferring the relative motion either lack robustness [4] or are unable to update the full set of camera parameters [15]. This section proposes the new intrinsic camera model for oblique-viewing endoscopes that is driven simultaneously by experiment and by the conceptual understanding of the optics arrangement. It is assumed that the probe rotates around an axis that is orthogonal to the image plane but not necessarily coincident with the optical axis. The parameters of the lens rotation required to update the camera model are estimated by a robust EKF that receives image information about the boundary contour and triangular mark as input. Our dynamic calibration scheme has two important advantages with respect to [15]: (i) the entire projection model is updated as a function of the lens rotation, and not only the RD profile curve; and (ii) the rotation of the lens can still be estimated in the absence of the triangular mark (see FIG. 1(b)). Convincing experimental results in re-projecting 3D points in the scene validates the approach.

In order to assess effect of the relative rotation between lens and camera-head in the camera model we acquired 10 calibration images while rotating the lens probe for a full turn. The camera calibration was estimated for each angular position using the methodology in section C, and both the boundary $\Omega$ and the triangular mark were located as described in section D and E. FIG. 8(a) plots the results for the principal point c, the boundary center w, and the lens mark p. Since the three parameters describe almost perfect concentric trajectories it seems reasonable to model the effect of the lens rotation on the camera intrinsics by means of a rotation around an axis orthogonal to the image plane. This idea has already been advanced by Wu et al. [3], but they consider that the axis always goes through the principal point, an assumption that in general does not hold, as shown by our experiment.

The scheme in FIGS. 5(b) and (c) aims to give the idea of the proposed model for describing the effect of the lens rotation in the camera intrinsics. Let us assume that the borescopic lens projects a virtual image onto a plane l' placed at the far end. We can think of l' as the image that would be seen by looking directly through a camera eyepiece. $K_c$ is the intrinsic matrix of this virtual projection, and c' is the point location where the optical axis meets the plane. Now assume that a camera head is connected to the eyepiece, such that the CCD plane l is perfectly parallel to l' and orthogonal to the optical axis. The projection onto l has intrinsic $K_h$, with the principal point c being the image of c'. So, if $K_h$ is the intrinsic matrix estimate $$K_0 \sim \begin{pmatrix} f & 0 & c_x \\ 0 & f & c_y \\ 0 & 0 & 1 \end{pmatrix}$$

then it can be factorized as $$K_0 \sim K_h K_c \sim \begin{pmatrix} f_h & 0 & c_x \\ 0 & f_h & c_y \\ 0 & 0 & 1 \end{pmatrix} \begin{pmatrix} f_c & 0 & 0 \\ 0 & f_c & 0 \\ 0 & 0 & 1 \end{pmatrix}$$

With $f_c$ being the focal length of the borescope lens, and $f_h$ being the focal length of the camera head that converts metric units into pixels.

Let us now consider that the lens probe is rotated around an axis 1 by an angle $\alpha$ (FIG. 8(c)). 1 is assumed to be orthogonal to the virtual plane l', but not necessarily coincident with the lens axis. In this case the point c' describes an arc of circle with amplitude $\alpha$ and, since 1 and l' are parallel, the same happens with its image c. The intrinsic matrix of the compound optical system formed by the camera head and the rotated borescope becomes $$K \sim K_h R_{\alpha,q'} K_c \quad (8)$$

With $R_{\alpha,q'}$ being a plane rotation by $\alpha$ and around the point q', where the axis 1, intersects l'.

$$R_{\alpha,q'} = \begin{pmatrix} \cos(\alpha) & \sin(\alpha) & (1-\cos(\alpha))q'_x - \sin(\alpha)q'_y \\ -\sin(\alpha) & \cos(\alpha) & \sin(\alpha)q'_x + (1-\cos(\alpha))q_y \\ 0 & 0 & 1 \end{pmatrix}, \quad (9)$$

The position of q' is obviously unchanged by the rotation, and the same is true of its image $q \sim K_h q'$. Taking into account the particular structure of $K_h$, we can re-write equation 8 in the following manner $$K \sim R_{\alpha,q} K_h K_c \sim R_{\alpha,q} K_0 \quad (9)$$

Figure 8:
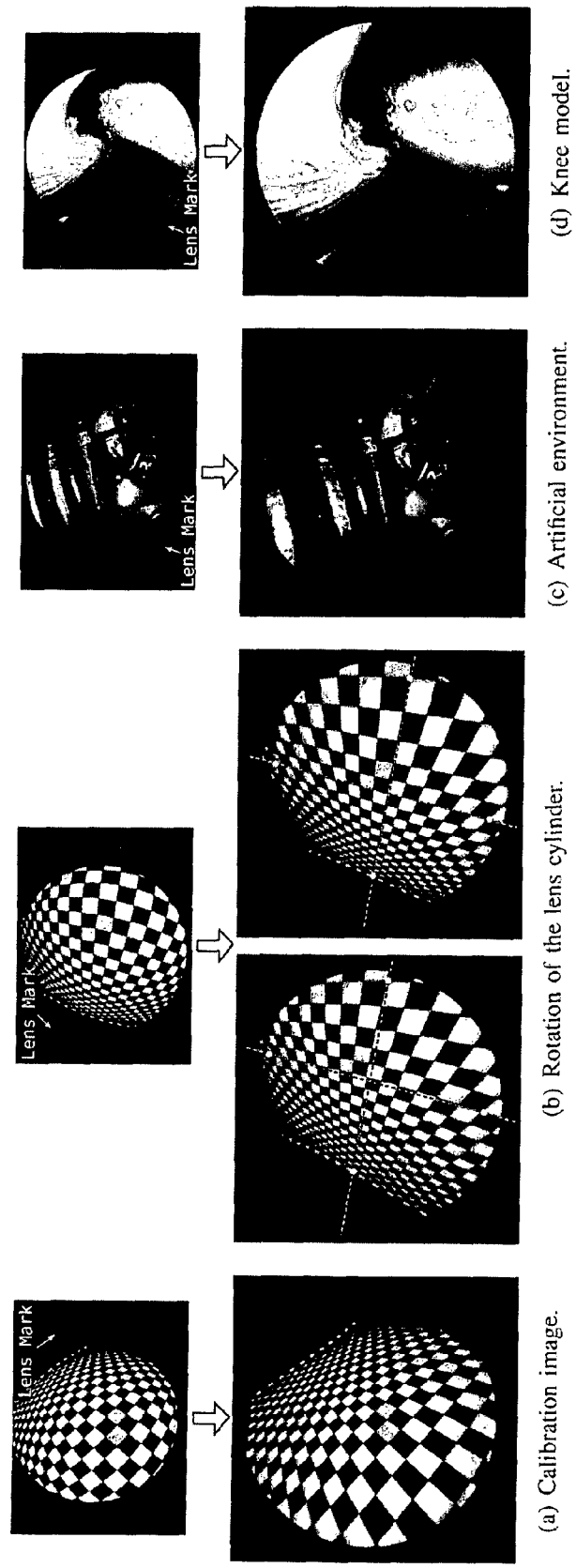
FIG. 8 shows the radial distortion correction of endoscopic video sequences with lens probe rotation. The original and warped frames are presented in the top and bottom rows, respectively. (a) shows the reference position (α=0) for which the initial calibration is performed. (b) compares the distortion correction results without (left) and with (right) compensation of the lens rotation motion. (c) and (d) are examples that illustrate the benefits of the RD correction in terms of perceiving the scene. The warped frames are larger because of the option to preserve the dimensions in the central image region.

We have just derived a projection model for the endoscopic camera that accommodates the rotation of the lens probe and is consistent with the observations of FIG. 8(*a*). The initialization procedure estimates the camera calibration $K_0$, $\xi$ at an arbitrary reference position ($\alpha=0$). At a certain frame time instant i, the matrix of intrinsic parameters becomes $$K_i \sim R_{\alpha_i, q_i} K_0 \quad (10)$$

Where $\alpha_i$ is the relative angular displacement of the lens, and qi is the image point that remains fixed during the rotation. Since the radial distortion is a characteristic of the lens, the parameter $\xi$ is unaffected by the relative motion with respect to the camera-head. Thus, from equation 2, it follows that a generic 3D point X represented in the camera coordinate frame is imaged at:

$$x \sim K_i \Gamma_\xi (I_3 0) X \quad (11)$$

The update of the matrix of intrinsic parameters at each frame time instant requires knowing the relative angular displacement $\alpha_i$ and the image rotation center $q_i$. We now describe how these parameters can be inferred from the position of the boundary contour $\Omega$ and the triangular mark p (section III).

Let $w_i$ and $w_0$ be respectively the center of the boundary contours $\Omega_i$ and $\Omega_0$ in the current and reference frames. Likewise, $p_i$ and $p_0$ are the positions of the triangular markers in the two images. We assume that both $w_i$, $w_0$ and $p_i$, $p_0$ are related by the plane rotation $R_{\alpha_i, \alpha_i}$ whose parameters we aim to estimate. This situation is illustrated in FIG. 6(*a*) where it can be easily seen that the rotation center qi must be the intersection of the bisectors of the line segments defined by $w_i$, $w_0$ and $p_i$, $p_0$. Once $q_i$ is known the estimation of the rotation angle $\alpha_i$ is trivial. Whenever the triangular mark is unknown (if it does not exist or cannot be detected), the estimation of qi requires a minimum of three distinct boundary contours (FIG. 6(*b*)).

In order to avoid under-constrained situations and increase the robustness to errors in measuring w and p, we use a stochastic EKF [12] for estimating the rotation parameters. The state transition assumes a constant velocity model for the motion and stationary rotation center. The equation is linear on the state variables $$\begin{pmatrix} \alpha_{i+1} \\ \dot{\alpha}_{i+1} \\ q_{i+1} \end{pmatrix} = \begin{pmatrix} T & 0_{2\times 3} \\ 0_{3\times 2} & I_3 \end{pmatrix} \begin{pmatrix} \alpha_i \\ \dot{\alpha}_i \\ q_i \end{pmatrix}$$

With T depending on the frame acquisition interval $\delta t$ $$T = \begin{pmatrix} 1 & \delta t \\ 0 & 1 \end{pmatrix}.$$

The measurement equation is nonlinear in $\alpha_i$ and $q_i$ $$\begin{pmatrix} w_i \\ p_i \end{pmatrix} = \begin{pmatrix} R_{\alpha_i, q_i} & 0_{3\times 3} \\ 0_{3\times 3} & R_{\alpha_i, q_i} \end{pmatrix} \begin{pmatrix} w_o \\ p_o \end{pmatrix},$$

with the two last equations being discarded whenever the detection of the triangular mark fails.

Figure 7:
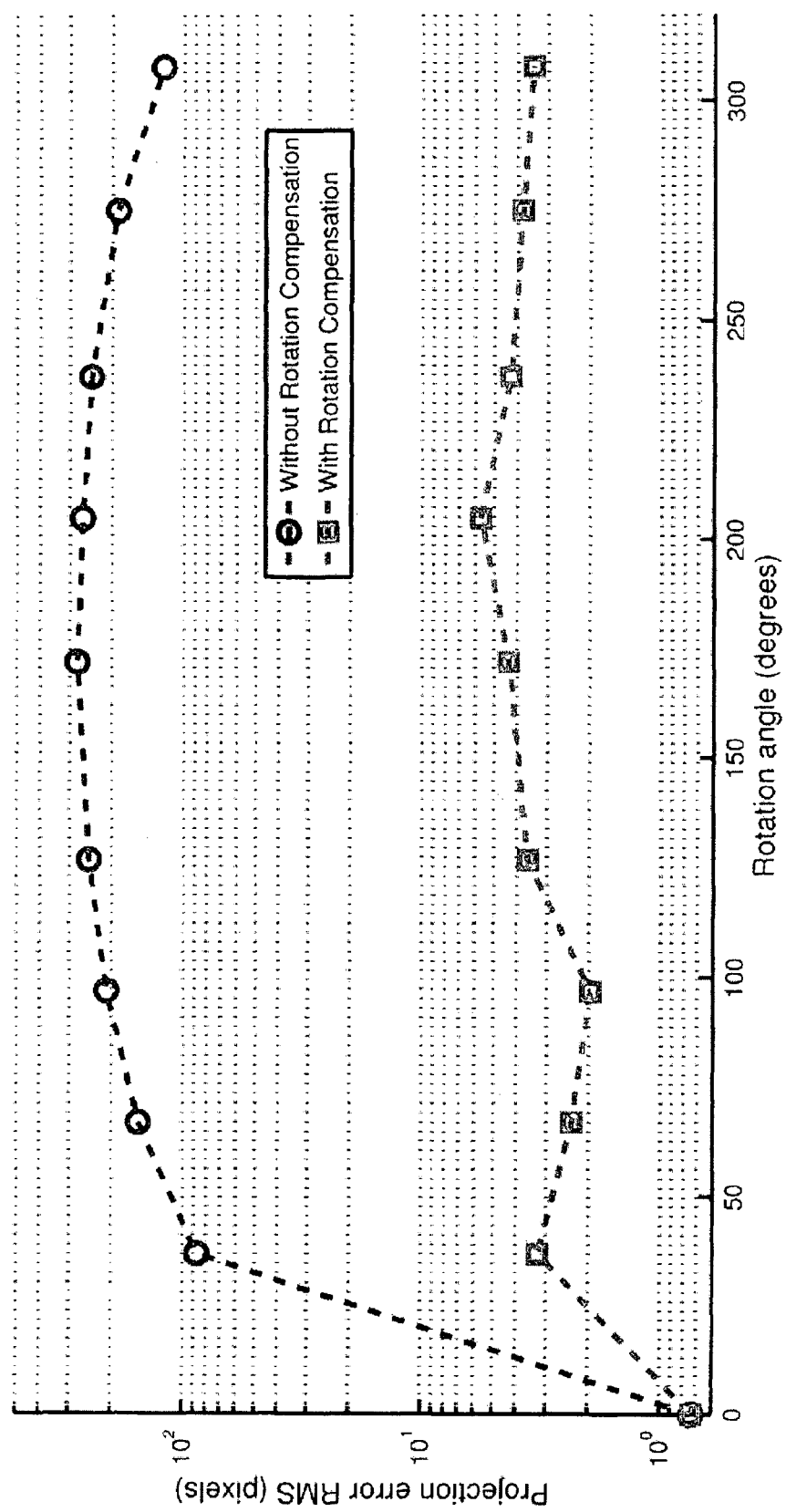
FIG. 7 shows the RMS reprojection error as a function of the angular displacement α. The blue line represents the error for the case of no rotation compensation (the values are the RMS displacement of the image corners). The red line shows the reprojection error when using our model (equation 11). For α=0 the plotted value is the reprojection error of the SIC calibration.

The proposed model was validated by re-projecting grid corners onto images of the checkerboard pattern acquired for different angles $\alpha$. The SIC calibration [21] was performed for the reference position ($\alpha=0$), enabling determination of the matrix K0, the RD parameter $\xi$, and the 3D coordinates of the grid points. Then, the camera head was carefully rotated without moving the lens probe in order to keep the relative pose with respect to the calibration pattern. The image rotation center $q_i$ and the angular displacement $\alpha_i$ were estimated for each frame using the geometry in FIG. 6. Finally, the 3D grid points were projected onto the frame using equation 11, and the error distance to the actual image corner locations was measured. FIG. 7 plots the RMS of the reprojection error for different angular displacements $\alpha$. The values vary between 2 and 5 pixels, but no systematic behavior can be observed. We only focused on the intrinsic parameters, while [2] and [3] consider both intrinsic and extrinsic calibration and employ additional instrumentation. Although no direct comparison can be made, it is worth mentioning that our reprojection error is smaller than [3] and equivalent to [2], where only points close to the image center were considered. From the above, and despite all conjectures, the results of the experiment clearly validate the proposed model.

G. Real Time Correction of the Radial Distortion Through Image Warping

This section discusses the rendering of the correct perspective images that are the final output of the visualization system. As pointed out in [7], the efficient warping of an image by a particular transformation should be performed using the inverse mapping method. Thus, we must derive the function F that maps points y in the desired undistorted image into points x in the original distorted frame. From equation 11, it follows that $$F(y) \sim K_i \Gamma_\xi (R_{-\alpha_i, q_i''} K_y^{-1} y).$$

$K_y$ specifies certain characteristics of the undistorted image (e.g. center, resolution), $R_{-\alpha_i, q_i''}$ rotates the warping result back to the original orientation, and q" is the back-projection of the rotation center $q_i$ $$q_i'' \sim (q_{i,x}'' q_{i,y}'' 1)^T \sim \Gamma_\xi^{-1} (K_i^{-1} q_i).$$

In order to preserve object's scale in the center region we expand the image periphery and keep the size of the undistorted center region. This is done by computing the size u of the warped image from the radius of the boundary contour of section D. Let rd be the distance between the origin and the point $K_{i-1} p_0$ (the distorted radius). The desired image size u is given by $u = f_{r_u}$, where f is the camera focal length, and $r_u$ is the undistorted radius. Accordingly, the matrix $K_y$ must be $$K_y \sim \begin{pmatrix} f & 0 & -f q_{i,x}'' \\ 0 & f & -f q_{i,y}'' \\ 0 & 0 & 1 \end{pmatrix}$$

with the center of the warped image being the locus where the image rotation center $q_i$ is mapped. FIG. 8 shows the RD correction results for some frames of an endoscopic video sequence. The examples clearly show the improvements in the scene's perception, and the importance of taking into account the lens probe rotation during the correction of the image geometry (FIG. 8(b)).

The rendering of the corrected images requires high performance computational resources to process data in real-time. We propose to parallelize parts of our algorithms for correcting the RD on the a parallel processing unit (in this case the GPU). We evaluate the impact of our hybrid serial+parallel solution by comparing 4approaches:

(i) a naive purely CPU based solution;
(ii) a hypothetical CPU version using OpenMP2directives [6], which can be used for shared-memory architectures, such as conventional COTS multicore CPUs of the x86 family.
(iii) an un-optimized hybrid CPU+GPU version and;
(iv) an optimized hybrid CPU+GPU version.

The experimental setup of the complete running system consists of a workstation equipped with an Intel®CoreTM2 Quad CPU at 2.40 GHz, 4 Gbyte of RAM and a GeForce 8800 GTX GPU. The GPU has 128 Stream Processors (SPs), each running at 1.35 GHz, and a total video RAM of 768 Mbyte. The source code was compiled with GCC version 4.3.4 and CUDA version 3.0 was used.

Figure 9:
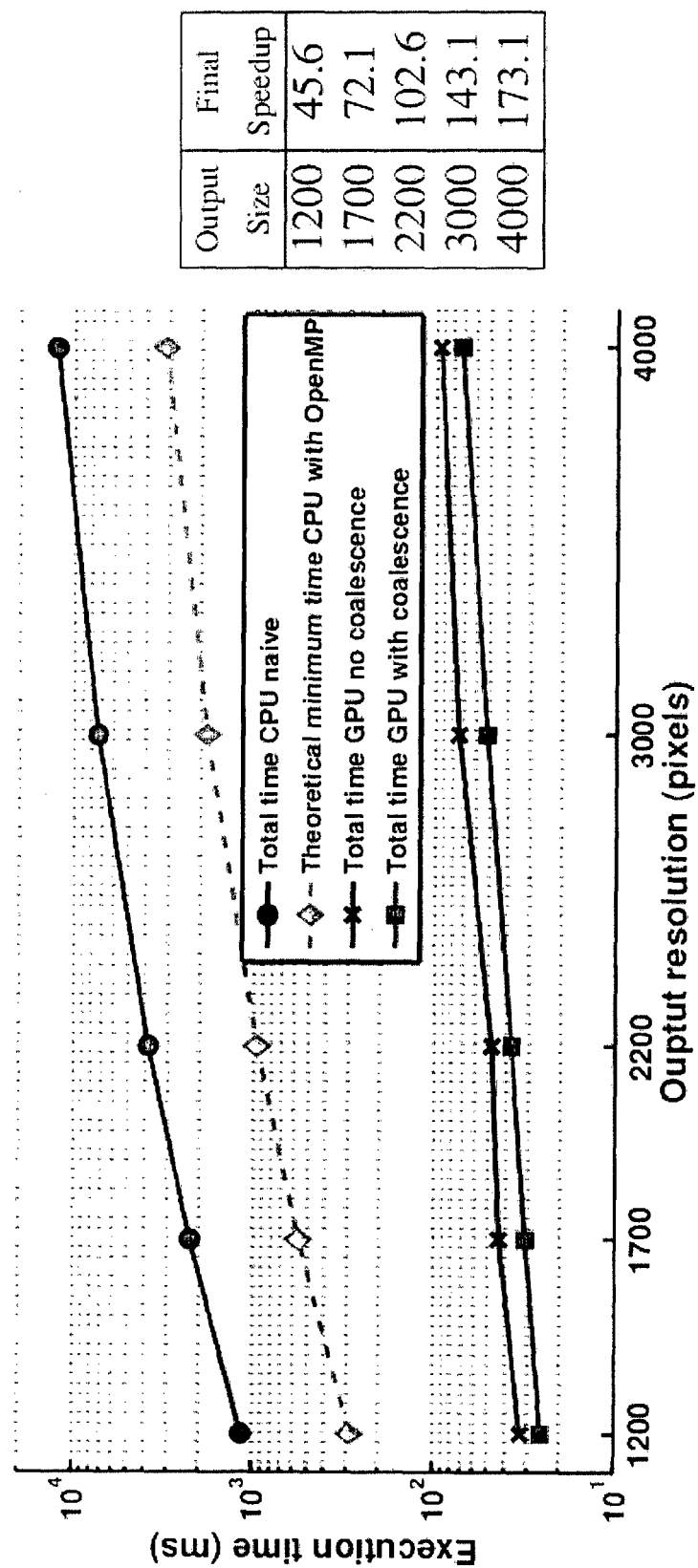
FIG. 9 shows the execution time per frame for different output image resolutions. The input images have a resolution of 1600×1200 pixels and the output images have variable square size. The table on the right shows the speedup achieved with the optimized hybrid CPU+GPU approach relative to the naive CPU solution.

FIG. 9 compares the execution times (required to process a single frame) achieved with the solutions mentioned above. The speedup table, a measure of how much faster the GPU is than the CPU, presents the ratio between the naive CPU and the optimized hybrid CPU+GPU execution times. The comparison given in FIG. 9 shows that the CPU is not able to handle large warping operations (the most time consuming task of the algorithms) as efficiently as the GPU. The table shows that for images with output sizes above 3000×3000 pixels not only the GPU accelerates execution, but also the CPU performance degrades due to the increase of cache miss penalties.

Figure 10:
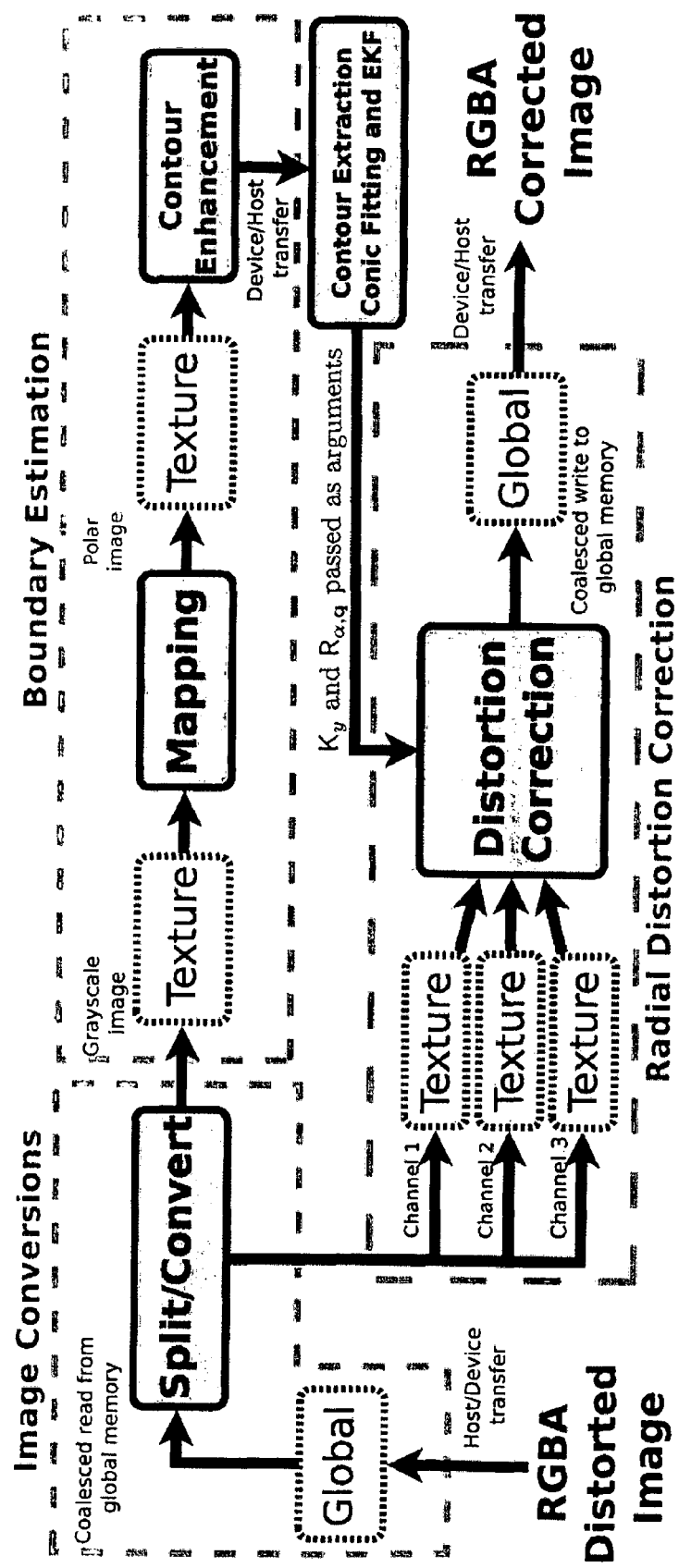
FIG. 10 shows the radial distortion correction algorithm steps for the particular case of an hybrid CPU+GPU computing unit. The red blocks represent CUDA kernels invocations. The green dotted blocks represent allocated device memory. Except for the purple block, which is computed on the CPU, all processing is performed on the GPU.

FIG. 10 presents the hybrid serial+parallel implementation steps of the radial distortion correction algorithm and the details of the implementation strategy adopted in the development of the hybrid program to execute on the CPU and GPU. The parallelization of the algorithms on the GPU is divided into three main steps:

(i) Image Conversions: the image is divided into its RGB channels and a grayscale conversion is performed.
(ii) Boundary Estimation: the grayscale image is bound to the parallel processing unit memory and the mapping to spherical coordinates (equation 1) along with the contour enhancement kernels are launched.
(iii) Radial Distortion Correction: the 3 image channels, from the Image Conversions stage, are bound to the parallel processing unit memory and the RD correction kernel is launched.

There is an intermediary step (isolated in FIG. 10) that is computed in the CPU. Each line of the polar image is scanned for the contour points to which the ellipse is fitted. The ellipse parameters are fed to the EKF discussed in section F and the calibration parameters are updated and passed as arguments to the distortion correction kernel. This step is implemented on the CPU rather than the GPU because of the serial nature of the processes involved.

The optimized hybrid CPU+GPU solution relies on a data pre-alignment procedure, that allows to perform a single memory access per group of threads, which is known by coalescence [1]. If the data to be processed by the GPU is misaligned instead, no coalesced accesses are performed and several memory transactions occur for each group of threads, reducing significantly the performance of the kernel under execution.

Although the alpha channel of the image is not being used, it is necessary to fulfill the memory layout requirement for performing fully coalesced accesses. An increase in the amount of data to be transferred introduces a penalty of 10.6% in the transfer time while the coalescence achieved reduces the kernels execution time by 66.1%. In sum, the coalesced implementation saves 38.7% of computational time relatively to the unoptimized hybrid CPU+GPU implementation.

The table of FIG. 12 presents the time taken by each step in FIG. 10 while processing a 150 frame video sequence (the times represent the mean time value of all frames processed for each resolution). The Image Conversions (I.C.) time also includes the transfer time of the input image from the host to the device's global memory. The Boundary Estimation (B.E.) time also considers the contour points' extraction, the ellipse fitting and the EKF estimation processes that are performed on the CPU (purple block in FIG. 14). Note that the mapping of the input image to the spherical space and the contour enhancement filter, both computed on the GPU, consume 1 to 3 milliseconds of the Boundary Estimation computational time represented in table II. The Radial Distortion Correction (R.D.C.) time also considers the transfer time from the device's global memory to the host.

REFERENCES

[1] D. Kirk and W.-m. Hwu, *Programming Massively Parallel Processors: A Hands-on Approach*. Morgan Kaufmann, 2010.
[2] T. Yamaguchi, M. Nakamoto, Y. Sato, Y. Nakajima, K. Konishi, M. Hashizume, T. Nishii, N. Sugano, H. Yoshikawa, K. Yonenobu, and S. Tamura, "Camera Model and Calibration Procedure for Oblique—Viewing Endoscope," in *MICCAI*, 2003, pp. 373-381.
[3] C. Wu, B. Jaramaz, and S. G. Narasimhan, "A Full Geometric and Photometric Calibration Method for Oblique-viewing Endoscope," *International Journal of Computer Aided Surgery*, vol. 15, pp. 19-31, 2010.
[4] N. Fukuda, Y. Chen, M. Nakamoto, and T, "A scope cylinder rotation tracking method for oblique-viewing endoscopes without attached sensing device," *Software Engineering and Data Mining*, no. 1, pp. 684-687, 2010.
[5] J. Barreto, J. Santos, P. Menezes, and F. Fonseca, "Ray-based Calibration of Rigid Medical Endoscopes," in *OMNIVIS*, 2008.
[6] B. Chapman, G. Jost, and R. Van Der Pass, *Using OpenMP: Portable Shared Memory Parallel Programming (Scientific Computation and Engineering Series)*. The MIT Press, 2008.
[7] L. Velho, A. C. Frery, and J. Gomes, *Image Processing for Computer Graphics and Vision*. Springer Publishing Company, Incorporated, 2008.
[8] R. I. Hartley and A. Zisserman, *Multiple View Geometry in Computer Vision*, 2nd ed. Cambridge University Press, ISBN: 0521540518, 2004.
[9] W. Smith, N. Vakil, and S. Maislin, "Correction of Distortion in Endoscope Images," *IEEE Transactions on Medical Imaging*, vol. 11, no. 1, pp. 117-122, January 1992.
[10] K. VijayanAsari, S. Kumar, and D. Radhakrishnan, "A new approach for nonlinear distortion correction in endoscopic images based on least squares estimation," *IEEE Transactions on Medical Imaging*, vol. 18, no. 4, pp. 345-354, 1999.
[11] J. Helferty, C. Zhang, G. McLennan, and W. Higgins, "Videoendoscopic distortion correction and its application to virtual guidance of endoscopy," *IEEE Transactions on Medical Imaging*, vol. 20, no. 7, pp. 605-617, 2001.
[12] S. M. Bozic, *Digital and Kalman Filtering*. London: Edward Arnold, 1979.
[13] J. P. Barreto, "A unifying geometric representation for central projection systems," *Comput. Vis. Image Underst.*, vol. 103, no. 3, pp. 208-217, 2006.
[14] A. Fitzgibbon, "Simultaneous linear estimation of multiple view geometry and lens distortion," in *CVPR*, vol. 1, 2001, pp. I-125-I-132 vol. 1.
[15] T. Stehle, M. Hennes, S. Gross, A. Behrens, J. Wulff, and T. Aach, "Dynamic Distortion Correction for Endoscopy Systems with Exchangeable Optics," in *Bildverarbeitungfür die Medizin* 2009. Berlin: Springer, 2009, 142-146.
[16] J.-Y. Bouguet. Camera Calibration Toolbox for Matlab. [Online]. Available: http://www.vision.caltech.edu/bouguetj/calib doc/index.html#ref
[17] Z. Zhang, "Flexible camera calibration by viewing a plane from unknown orientations," in *ICCV*, 1999, pp. 666-673.
[18] R. Shahidi, M. Bax, C. Maurer, J. Johnson, E. Wilkinson, B. Wang, J. West, M. Citardi, K. Manwaring, and R. Khadem, "Implementation, calibration and accuracy testing of an image-enhanced endoscopy system,"*IEEE Transactions on Medical Imaging*, vol. 21, no. 12, pp. 1524-1535, January 2002.
[19] C. Wengert, M. Reef f, P. Cattin, and G. Sź ekely, "Fully automatic endoscope calibration for intraoperative use," in *Bildverarbeitungfür die Medizin* 2006, 2006, pp. 419-423.
[20] J. Mallon and P. F. Whelan, "Which pattern? Biasing aspects of planar calibration patterns and detection methods," *Pattern Recognition Letters*, vol. 28, no. 8, pp. 921-930, January 2007.
[21] J. Barreto, J. Roquette, P. Sturm, and F. Fonseca, "Automatic Camera Calibration Applied to Medical Endoscopy," in *BMVC*, 2009.
[22] S. D. Buck, F. Maes, A. D'Hoore, and P. Suetens, "Evaluation of a novel calibration technique for optically tracked oblique laparoscopes," *Proceedings of the 10th international conference on Medical image computing and computer-assisted intervention-Volume Part I*, pp. 467-474, 2007.
[23] A. Fitzgibbon, M. Pilu, and R. Fisher, "Direct least square fitting of ellipses," *IEEE Transactions on Pattern Analysis and Machine Intelligence*, vol. 21, no. 5, pp. 476-480, May 1999.
[24] M. A. Fischler and R. C. Bolles, "Random Sample Consensus:
A Paradigm for Model Fitting with Applications to Image Analysis and Automated Cartography," *Commun. ACM*, vol. 24, no. 6, pp. 381-395, 1981.

The invention claimed is:

1. An apparatus for camera calibration comprising the following:
    (i) a calibration box (1) made of opaque materials for avoiding the entrance of light from the exterior, and having one or more openings (2) for allowing access to a lens probe, each opening being surrounded by a rubber membrane (3) that minimizes the entrance of light from the exterior; the box is divided in two compartments by a separator (6) in transparent or translucent material, an open compartment that can be filled with a fluid for replicating the means where the visual inspection will be carried;
    (ii) a planar grid (7) with a known pattern, made of transparent or translucent material, which is placed on the top of the separator;
    (iii) a light source, installed in the lower box compartment (5), for diffuse back-illumination of the planar grid;
    (iv) a computer unit, with sequential and parallel processing capabilities, comprising a Central Processing Unit and/or a Graphics Processing Unit, that is connected to a camera for image acquisition of a single image of the known pattern;
    the acquired image used as an input to perform camera calibration;
    (v) a display device connected to the computer unit;
    (vi) and an interface device connected to the computer unit for entering user commands.

2. The apparatus of claim 1 which includes a planar checkerboard pattern that is viewed by said camera and that can eventually include distinguishable features, centered in two consecutive diagonal white squares, which identify the grid corner lying in between.

3. The apparatus of claim 1 which can include multiple possible entry points for observing the planar pattern, these entrance points can have multiple shapes and sizes according to the types of lens probe and for the viewing of the pattern from different perspectives.

4. A method for automatic camera calibration such as in medical or industrial devices like endoscopic cameras, a projection model updating according to the lens probe rotation, and a real-time image distortion correction that carries out the following operations:
    (i) user command acquisition of one or more calibration images of a checkerboard pattern using a calibration box;
    (ii) detection of the grid corners in the calibration images and establishment of image-plane correspondences;
    (iii) determination of a camera's intrinsic parameters such as focal length, principal point, skew and aspect ratio and the lens distortion, using the image-plane correspondences in at least one of the calibration images;
    (iv) continuous image/video acquisition;
    (v) detection, when applicable, of a boundary contour between circular and frame image regions, and image coordinates of a triangular mark, this operation being carried out at each frame time instant;
    (vi) robust determination, when applicable, of an angular displacement undergone by a lens probe with respect to camera head using output of (v);
    (vii) updating intrinsic calibration information given an initial camera calibration of (iii) and, when applicable, a relative rotation information of (vi), making use of a new projection model for describing oblique viewing endoscopes or other camera device where a lens probe rotates with respect to a camera-head; and
    (viii) performing real-time image rectification for correction of radial distortion using the current camera calibration of (vii).

5. The method of claim 4 wherein the operation (ii) consists of an automatic establishment of the correspondence between corner points in the planar grid with a known pattern (7), which is a checkerboard pattern, and corner points in one of the calibration images, and comprises the following steps:

a. detection of corners or seed points in a central image region using image processing techniques;
b. inference of coordinates of the corners or seed points in the planar grid with a known pattern which is a checkerboard pattern;
c. determination of the function that maps the corner or seed points in planar grid coordinates with a known pattern (7) which is a checkerboard pattern into points in image coordinates, with implicit encoding of the camera parameters, the lens distortion, and the relative rotation and translation between the planar grid with a known pattern which is a checkerboard pattern and the camera;
d. projection of the planar grid corners with a known pattern (7) which is a checkerboard pattern into the calibration image using the function determined in (c);
e. localization of new corners in the image through local search around projected corners from the planar grid with a known pattern (7) which is a checkerboard pattern; and
f. iteration over steps (c) to (e) until the number of established corner correspondences is considered satisfactory.

6. The method of claim 4 wherein the operation (iii) consists of an estimation of the camera intrinsic parameters and lens distortion from a single calibration image using the corner correspondences comprising the following steps:
a. computation of a function that maps lifted point coordinates in the planar grid with a known pattern (7) into lifted point coordinates in the image plane; and
b. decomposition of the mapping function of (a) for determining the focal length, principal point, aspect ratio, skew, distortion parameters, and relative rotation and translation, between planar grid with a known pattern (7) and camera.

7. The method of claim 6 which can be complemented by an additional step of iterative non-linear optimization for achieving one, or more than one, of the following objectives:
a. refinement of the estimated parameters, and
b. fusion of the estimates provided by different calibration images.

8. The method of claim 4 wherein the operation (v) comprises the unsupervised real-time tracking of the boundary contour of the Circular Image region and detection of the triangular mark (if visible) and comprises the following steps:
a. definition of a ring area in an original image, partially or totally containing a last estimate of the boundary contour of the circular image region;
b. rendering of a new stripe image where a previously estimated boundary contour is mapped into the central vertical line;
c. detection of boundary points in the stripe image using image processing technique;
d. mapping of the detected points back into the original image and fitting of a conic curve using robust estimation;
e. repetition of steps (a) to (d) until the boundary contour estimate converges; and
f. robust detection of the triangular mark by scanning an auxiliary vertical line in the stripe image slightly deviated to the right, selecting a pixel location that has maximum intensity, and mapping back the pixel location to the original image.

9. The method of claim 8 wherein the operation (vi) of the estimation, when the lens probe undergoes rotation motion, of the angular displacement with respect to the lens position for acquiring the calibration images, defined as reference position, making use of the boundary contour and the triangular mark, when available, obtained for the reference position, and of the continuous acquisition of the video, that for a current image comprises the following steps:
a. detection of the boundary contour and the triangular mark; and
b. feeding of the information of (a) into a stochastic filter that infers a current angular displacement, thus, a relative rotation of the lens probe being determined using exclusively image information.

10. The method of claim 9 wherein the operation (vii) comprises, when the lens probe undergoes rotation motion, given a camera intrinsic calibration at the initial reference position, and the current angular displacement of the lens probe with respect to that reference position, inferring the camera intrinsic calibration and projection model for the current image, including focal length, principal point, aspect ratio, skew and distortion parameters.

11. The method of claim 4 wherein the operation (viii) which comprises a real time correction of the radial distortion through image warping, based on parallel processing and making use of conventional computational unit systems, the method comprising:
a. transference of data from the host computational unit to the parallel processing unit;
b. processing of images on the system parallel processing unit;
c. transference of the final processed images back to the host computational unit; and
d. visualization of results.

12. A computer program embodied on a non-transitory computer readable storage medium which, when executed by a processor, performs the method of claim 4.

13. The method of claim 8 which is accelerated using the parallel computational capabilities of the parallel processing unit.

14. The method of claim 4 wherein operation (iii) is performed with a single calibration image.

15. The method of claim 4 used for complete geometric calibration of optical devices.

16. The method of claim 4 further comprising determining parameters of a suitable mapping function that assigns to each pixel of an image a 3D direction of corresponding incident light.

* * * * *